United States Patent
Pauli

(10) Patent No.: US 10,391,004 B2
(45) Date of Patent: Aug. 27, 2019

(54) COMPOSTABLE DIAPER AND METHOD OF MANUFACTURING THEREOF

(71) Applicant: ZERI Europe—Foundation for a Blue Economy vzw, Oudergem (BE)

(72) Inventor: Gunter Pauli, Kamakura Kanagawa (JP)

(73) Assignee: ZERI Europe—Foundation for a Blue Economy vzw, Oudergem (BE)

( * ) Notice: Subject to any disclaimer, the term of this patent is extended or adjusted under 35 U.S.C. 154(b) by 228 days.

(21) Appl. No.: 15/332,891

(22) Filed: Oct. 24, 2016

(65) Prior Publication Data

US 2017/0112687 A1    Apr. 27, 2017

(30) Foreign Application Priority Data

Oct. 25, 2015 (EP) ..................... 15003048

(51) Int. Cl.
| | |
|---|---|
| *A61F 13/53* | (2006.01) |
| *A61F 13/505* | (2006.01) |
| *A61F 13/15* | (2006.01) |
| *A61L 15/62* | (2006.01) |
| *A61F 13/49* | (2006.01) |

(Continued)

(52) U.S. Cl.
CPC ........ *A61F 13/53* (2013.01); *A61F 13/15252* (2013.01); *A61F 13/15585* (2013.01); *A61F 13/49* (2013.01); *A61F 13/505* (2013.01); *A61L 15/62* (2013.01); *B32B 5/022* (2013.01); *B32B 21/08* (2013.01); *B32B 37/06* (2013.01); *A61F 2013/1526* (2013.01); *A61F 2013/49098* (2013.01); *A61F 2013/530007* (2013.01); *A61F 2013/530343* (2013.01); *A61F 2013/530364* (2013.01); *A61F 2013/842* (2013.01);

(Continued)

(58) Field of Classification Search
CPC ........ A61F 13/15252; A61F 2013/1526; A61F 2013/530364; A61F 13/53–539; A61F 2013/530007; A61F 2013/530343; A61F 2013/842; A61L 15/62
See application file for complete search history.

(56) References Cited

U.S. PATENT DOCUMENTS

| | | | |
|---|---|---|---|
| 2001/0014797 A1* | 8/2001 | Suzuki | A61F 13/15211 604/378 |
| 2005/0035327 A1* | 2/2005 | Canada | A61L 15/44 252/182.15 |

(Continued)

FOREIGN PATENT DOCUMENTS

| | | |
|---|---|---|
| EP | 0 811 390 A1 | 12/1997 |
| KR | 1999/0064932 A | 8/1999 |
| WO | WO 98/10725 A1 | 3/1998 |

OTHER PUBLICATIONS

Extended European Search Report dated Apr. 13, 2016, for European Application No. 15003048.4-1308.

*Primary Examiner* — Susan S Su

(74) *Attorney, Agent, or Firm* — Cook Alex Ltd.

(57) ABSTRACT

A diaper comprising a biodegradable top sheet, a biodegradable absorbent core and a biodegradable bottom sheet, wherein the bottom sheet is liquid impervious and wherein the top sheet is configured for transmission of bodily fluids to the absorbent core. The absorbent core comprises a first and a second non-woven layer comprising pulp fibers, and in between thereof a composting-stimulating layer comprising charcoal.

19 Claims, 1 Drawing Sheet

(51) Int. Cl.
*B32B 5/02* (2006.01)
*B32B 21/08* (2006.01)
*B32B 37/06* (2006.01)
*A61F 13/84* (2006.01)

(52) U.S. Cl.
CPC . *B32B 2262/067* (2013.01); *B32B 2307/7265* (2013.01); *B32B 2555/02* (2013.01)

(56) References Cited

U.S. PATENT DOCUMENTS

| | | |
|---|---|---|
| 2009/0299313 A1 | 12/2009 | Knightingale et al. |
| 2010/0022978 A1* | 1/2010 | Kasai ................ A61F 13/15658 604/367 |
| 2013/0237933 A1* | 9/2013 | Ko ...................... A61F 13/2051 604/286 |
| 2015/0094672 A1* | 4/2015 | Blucher ................ A61L 15/325 604/304 |
| 2015/0190290 A1 | 7/2015 | Park |
| 2015/0216742 A1* | 8/2015 | Johnson .............. A61F 13/8405 604/359 |

\* cited by examiner ial application claims priority to and the benefit
COMPOSTABLE DIAPER AND METHOD OF MANUFACTURING THEREOF

CROSS REFERENCE TO RELATED APPLICATION

This patent application claims priority to and the benefit of EP Application No. 15003048.4, filed on Oct. 25, 2015, the contents of which are incorporated herein by reference.

FIELD OF THE DISCLOSURE

The present disclosure relates to a compostable diaper comprising comprising a biodegradable topsheet, a biodegradable absorbent core and a biodegradable bottom sheet, wherein the bottom sheet is liquid impervious and wherein the top sheet is configured for transmission of bodily fluids to the absorbent core.

The present disclosure further relates to a method of manufacturing such diaper comprising the laminating of the bottom sheet, the top sheet and the absorbent core.

The present disclosure further relates to a method of disposing a used diaper containing urine and/or another bodily fluid, wherein the diaper is at least partially disposed by composting.

BACKGROUND

Single-use, disposable diapers have become a major source of waste. It is known that the disposable diapers are good for approximately 6% of the waste volume of a city. When disposed in a landfill, this leads to the production of methane, strongly contributing to warming up of the atmosphere. When burned, there is merely little recovery of the energy spent for production of these diapers.

In the light hereof, new compostable diapers have been designed and marketed. These diapers have the advantage of being single use, such that there is no need of washing them. However, the diapers can be converted, at least partially into fertile material. One such compostable diaper is known from EP0525245A1. It is observed therein that a conventional disposable absorbent product consists of about 80% of compostable material, such as wood pulp fibers. In the composting process, the articles are shredded and commingled with organic waste prior to the composting per se. After composting is complete, the non-compostable particles are screened out. Since the amount of non-compostable particles was too high, EP0525245 disclosed a product with a liquid impervious backsheet comprising a compostable polymer. This backsheet thereto contained a flexible starch based film. The preferred topsheet contained staple-length propylene fibers with a length of at least about 15 mm. A more recent embodiment of such a biodegradable liquid impervious backsheet, comprising a laminate of films, is for instance known from WO2013/137817. Biodegradable and compostable liquid permeable top sheets are also known. Alternatively, use can be made of biodegradable, liquid impervious top sheets with one or more openings.

Still, improvements to compostable diapers are desired. Particularly, composting of diapers will only make sense on a large scale, if the composting process does not need a long duration in order to arrive at a compost that has any commercial value. Moreover, in the light thereof, any processing on the diapers such as shredding and combining them with other materials, tends to lower economic viability due to labour costs.

BRIEF DESCRIPTION OF THE DRAWINGS

These and other aspects of the diaper and its manufacturing method will be further elucidated with reference to the figures, wherein.

SUMMARY

Figure 1:
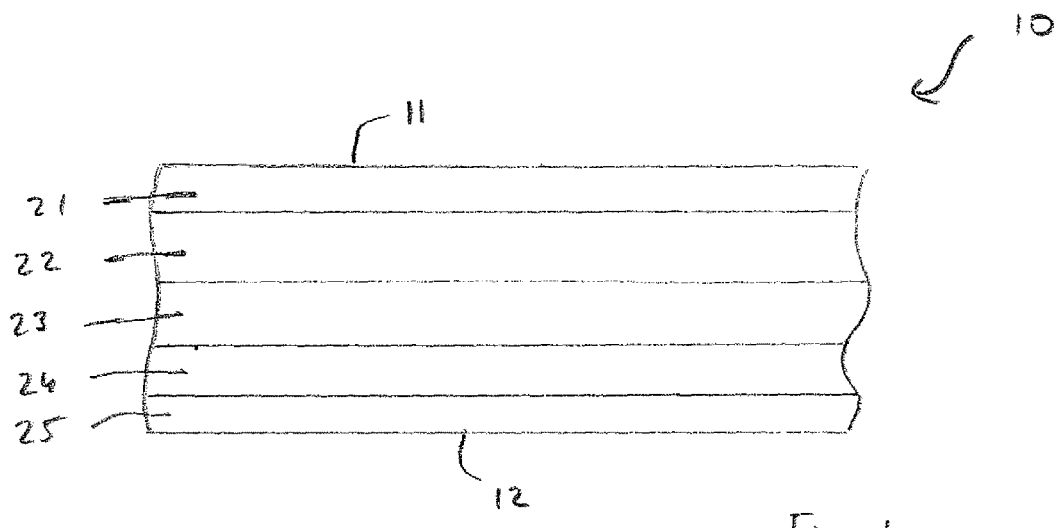
FIG. 1 schematically shows a cross-sectional view of a laminate for use as or in a diaper.

It is therefore an object of the subject matter disclosed herein to provide an improved disposable diaper that is compostable in a manner that is economically viable.

Further objects relate to the manufacture of such diaper and its disposal by composting, in a manner that is economically viable.

In one aspect, a diaper is provided that comprises a biodegradable topsheet, a biodegradable absorbent core and a biodegradable bottom sheet, wherein the bottom sheet is liquid impervious and wherein the top sheet is configured for transmission of bodily fluids to the absorbent core. Herein, the absorbent core comprises a first and a second non-woven layer comprising pulp fibers, and in between thereof a composting-stimulating layer comprising charcoal.

In another aspect, a manufacturing method is provided, comprising the steps of providing on top of each other a biodegradable, liquid impervious backsheet, a film or sheet of non-woven pulp fibers, a composting-stimulating film or sheet comprising charcoal, another film or sheet of non-woven pulp fibers, and a biodegradable and particularly liquid pervious topsheet. Herein said sheets and films are laminated together to form a diaper.

In again another aspect, the present disclosure relates to the disposal of the diaper described herein in a composting process. More particularly, a method of creating active humus with a carbon content of at least 20% is provided, by means of composting used diapers that contain urine and/or another bodily fluid, wherein the diapers of the present dislcosure are used.

It has been found in investigations leading to the present disclosure that the compostability of a diaper can be substantially improved by means of integrating a composting-stimulating layer comprising active carbon, embodied as charcoal, into the absorbent core of the diaper. Herewith, it appears no longer necessary to process used diaper prior to composting them, i.e. by shredding and mixing. Rather, the diapers may be collected into a composting basket, and will then be biodegraded by themselves. It has been found, in various preliminary tests, that the composting process may therewith be accelerated, such that the compost may be ready within a year or even within six months. Furthermore, the resulting compost has been found to be rich in carbon, i.e. and is considered active humus rather than just any compost.

Compost is generally defined as organic matter in a purposeful state of partial decomposition. Particularly, when shredded diapers are mixed with other sources, the overall composting time is dependent on a plurality of factors. On average, the output quality will reduce. Compost generally has a relatively low carbon content. Active humus on the other hand is organic matter that has reached a fairly complete decomposition stage and has a higher carbon content, of at least 20% and suitably 30-40%.

The charcoal in the diaper disclosed herein increases the carbon content, but also turns out to accelerate composting. This is deemed the result of the presence of a porous structure in charcoal, which constitutes a suitable location for microorganisms and which enables diffusion of gases such as oxygen towards the microorganisms. Furthermore, it has been found that a suitable amount of charcoal can be integrated into the diaper in that a separate sheet or film is provided, rather than coating fibers of the first and second layers with charcoal. Suitably, the surface area per gram of material of charcoal is chosen in the range from 40 to 1400 square meters, for instance in the range of 60-600 square meters/gram, more particularly 100-400, or even 200-400 square meters/gram, as measured by the BET method for determining specific surface area. The complex internal surface area is usually divided into three components. Channels and pores with diameters less than 2 nm (micropores) generally contain the largest portion of the carbon's surface area; pores with diameters between 2 and 50 nm are known as mesopores, and pores with diameters greater than 50 nm are defined as macropores. Charcoal porosity varies primarily as a function of feedstock and secondarily as a function of pyrolysis conditions.

The charcoal suitably has an average particle size in the range of 10-50 microns and more preferably 20-30 microns. Such particle size enables processing into a sheet and provides an advantageous surface area, in addition to accessibility of pore structures with pore diameters in the micrometer range (for instance up to 20 microns). One beneficial source for charcoal with such a structure is wood charcoal, and more preferably bamboo charcoal. If so desired the bamboo charcoal may be mixed with charcoal from other sources, including for instance charcoal from cypresses and/or coconuts.

In a suitable embodiment, the composting-stimulating layer is present in an amount of 8-30 wt % based on the total diaper. The exact amount of charcoal will further depend on the size of the diaper. For a baby, the total diaper weight may be in the range of 50 grams. For an older child, the weight may be 150 gram. The use of composting-stimulating layer(s) with a total weight up to approximately 100 gram per diaper is foreseen. Clearly, the composting-stimulating layer may herein be arranged either as a single layer, or in the form of a plurality of layers. In case of a plurality of layers is present, one such layer is suitably arranged between a first and a second layer of non-woven material.

In a further embodiment, the composting-stimulating layer further comprises a fiber material. Suitably, a non-woven fiber material is present. Preferably, the non-woven fiber material comprises fibers of a type corresponding to that of at least one of the layers of non-woven material. This is deemed beneficial for adhesion, but also for composting. Most suitably, as will be explained hereinafter, the fiber material is based on reed pulp, rather than wood pulp, and preferably comprises bamboo fibers. The amount of such fibers in the composting-stimulating layer is suitably at most 30%.

In again a further embodiment, the composting-stimulating layer further comprises coffee grounds. The addition of this type of material turns out suitable for the removal of odors. Furthermore, it is deemed a good method for ensuring the provision of sufficient organic material. However, the addition of coffee grounds is not explicitly necessary. The coffee is particularly roasted coffee. Suitably, use is made of caffeine-free coffee grounds, in order to prevent negative impact on sensitive skins. The coffee grounds may be added in an amount of 10-30% relative to the charcoal.

The first and second non-woven layers preferably contain a fluff material. Fluff material are known as fibers that typically have a moisture content of less than 10% and are of a hydrophilic nature. Fluff pulps are typically processed into non-wovens by means of dry-laying processes, such as air laying, spunbonding, hydroentangling. Suitably, the non-wovens are dried in a continuous sheet form and wound onto rolls. It will be understood that the pulp fibers are the primary elements of the non-woven layers. Other elements may be added, as known per se. Suitably, the first non-woven layer, which is arranged adjacent to the top sheet, comprises fiber particles (the fluff) with an average particle size that is smaller than the second non-woven layer. The smaller particle size of the first non-woven layer is found to contribute to distribution of urine and/or other bodily fluids through the diaper. The larger particle size of the particles in the second non-woven layer is deemed beneficial to increase moisture absorption. Thus, in this manner, urine is removed from the user's skin quickly. In one suitable embodiment, the average particle size in the first non-woven layer is less than 3 mm, suitably at most 2 mm, preferably at most 1 mm. In a further embodiment, the average particle size in the second non-woven layer is in the range of 1-5 mm, preferably 1.5-3.0 mm. In again a further embodiment, the said maximum values may be obtained by sieving, such that the non-woven layers are substantially free of particles with a larger diameter. The fluff material may further be sieved so as to remove particles with too small diameter, for instance of less than 0.1 mm. Such particles could easily agglomerate due to their comparatively large surface area, and particularly upon wetting. This leads to undesired effects, also in the process of composting.

The fibers in the first and the second non-woven material are preferably, at least partially bamboo fibers. Bamboo is a reed material that grows quickly and still is sufficiently hard. If desired for softness, other fibers, such as wood pulp fibers could be added. Bamboo is the common term for members of a particular taxonomic group of large woody grasses (subfamily Bambusoideae, family Andropogoneae/Poaceae).

In view of the compostability, the diaper of the present disclosure is suitably free of materials that are not compostable and preferably also of materials that are merely compostable over a long period in time. Thus, the diaper is suitably free of conventional absorbent materials, such as superabsorbent polymers. Preferably, the diaper does not contain any adhesive strips or the like for adhesion and fitting. Rather, the diaper is preferably used in combination with a reusable, washable fabric that fits the user. The diaper will then be connected to this fabric. This combination is known per se in the art. However, it is not excluded that the absorbent core is used in combination with non-compostable sheets, or that the absorbent core further contains additives, such as the said super absorbent polymers.

The top sheet and the bottom sheet of the diaper are preferably chosen in accordance with known technology, such as for instance specified in WO2013/137817A1 that is included herein by reference. The diaper may be designed in a variety of forms and models, which are known per se to a skilled person in the art of diaper design.

In the composting process, the diapers are suitably collected into a composting basket without need for any preceding pre-treatment such as shredding or mixing with other fibers. This simplifies processing and therewith reduces cost thereof. In one further embodiment, fungi may be added to the diapers for increasing the composting process. However, it is deemed that the urine, other bodily fluids and/or feces itself contain sufficient microorganisms for starting the composting process. Furthermore, when collected in a basket, the basket may contain a culture of microorganisms that may spread into the diapers. In one implementation, the fungi could for instance be present in a home box in which parents may collect the diapers. Said home box may then be brought to a location in which the composting process takes place.

DETAILED DESCRIPTION OF ILLUSTRATED EMBODIMENTS

FIG. 1 shows in a schematical cross-sectional view a laminate 10 for use as or in a diaper structure. The drawing of laminate 10 is not drawn to scale and merely intended for illustrative purposes. The laminate 10 is provided with a first side 11 and a second side 12. The first side 11 is configured to be the side from which urine or another bodily fluid is absorbed into the diaper structure. The laminate comprises a composting-stimulating layer 23 that is present between a first and second layer 22, 24 of non-woven pulp fibers. At the first side 11, the laminate 10 is covered with a biodegradable liquid pervious top sheet 21. At the second side 12, the laminate 10 is covered with a biodegradable liquid impervious backsheet 25.

While the individual layers 21-25 are herein shown to have a uniform thickness, this does not need to be the case. For instance, the first and second layer of non-woven pulp fibers 22, 24 may be provided with zones having an increased thickness, so as to increase comfort to a user. Additionally, the laminate is laminated together, which may occur at predefined areas. Such predefined areas may further be, but need not be, suitable for a separation process, i.e to separate the laminate into a plurality of diapers. For sake of simplicity, such predefined lamination areas have not been shown in FIG. 1.

Figure 2:
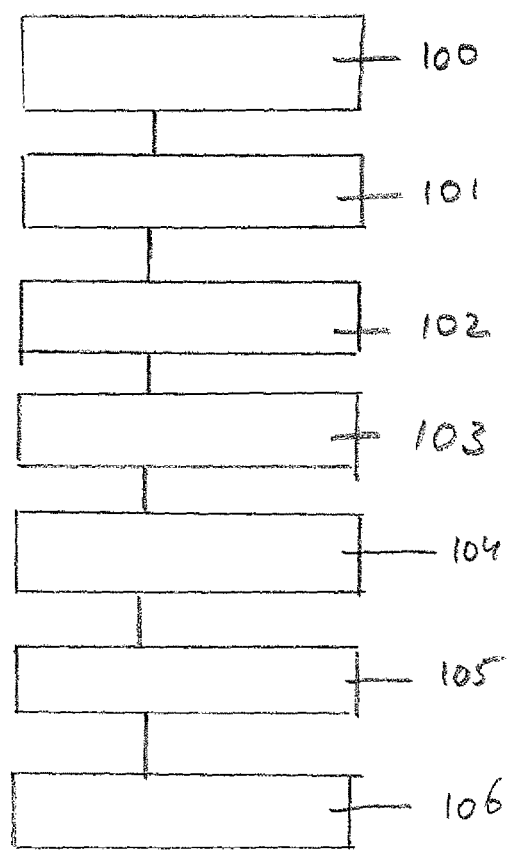
FIG. 2 shows a flow diagram for manufacturing a diaper.

FIG. 2 shows a process flow for preparation of the diaper material as shown in FIG. 1. The laminate 10 is typically prepared in a lamination process comprising a plurality of steps 100-105. In a first step 100, a backsheet 25 is provided, which is biodegradable and liquid impervious. For instance, the liquid impervious sheet 25 may contain a biodegradable polymer material chosen among polyhydroxyalkanoates, aliphatic polyester-based polyurethanes, polylactides, polycaprolactones, poly(vinyl alcohol) compositions, hydroxypropylcellulose, cellulose esters, starch based polymers based on wheat starch, potato starch, rice starch or corn starch, and interpenetrating networks copolymers and/or blends therewith. It is not excluded that this sheet 25 is mixed with a tissue paper, such as wet-laid cellulosic tissue paper, for instance a non-woven fabric.

In a second step 101, a second layer 24 of non-woven pulp fibers is provided. In a most suitable embodiment, this second layer 24 contains a fluff material. Preferably, the fluff material contains bamboo, for instance with a bamboo content of at least 40%, more preferably at least 60%, or at least 80% or even more to be substantially of bamboo. Suitably, the fluff material has been processed, prior to the lamination process, into a non-woven sheet. It is not excluded that a plurality of such non-woven sheets is provided into the laminate. Particularly, if locally a larger thickness is required, such further sheet may be provided and may thereafter be patterned using a suitable patterning process, such as punching or cutting.

In a third step 102, the composting-stimulating layer 23 is applied. This composting-stimulating layer 23 is suitably provided in the form of sheet comprising charcoal particles and a fiber material, such as a non-woven fiber material comprising bamboo material. Furthermore, in a most preferred embodiment, the composting-stimulating layer 23 further comprises coffee grounds. Rather than using a preprocessed sheet that comprises both coffee grounds and charcoal material, it is not excluded that the coffee grounds are added during lamination, for instance in the form of a spray process. Alternatively, the coffee grounds may be integrated in one of the first layer 22 and the second layer 24 of non-woven material, or may be inserted as a separate sheet, for instance in the form of a blend with non-woven material. In one preferred implementation, the composting-stimulating layer 24 is applied in the form of a plurality of layers, so as to increase the density of charcoal and/or coffee grounds. In such an implementation, each layer comprising charcoal is suitably present between layers of non-woven fiber material. The coffee grounds may then be present in such layers of non-woven material, in the layer containing the charcoal, or be provided in powder form. The amount of coffee grounds is suitably merely 10-30% by weight relative to the charcoal. This weight ratio enables integration of the coffee grounds into and/or between one or more of said layers in several manners.

In a fourth step 103, a first layer 22 of non-woven material is provided. The material suitably corresponds to that of the second layer 24 of non-woven material.

In a fifth step 104, a liquid pervious top sheet 21 is provided. Examples include a plastic film, a nonwoven material coated with a liquid impervious material, or a hydrophobic nonwoven material. The top sheet may be breathable so as to allow vapour to escape from the composting-stimulating layer, while still preventing liquids from passing therethrough. Examples of breathable materials are porous polymeric films and nonwoven fabrics from spunbound and meltdown fibers. Rather than being entirely liquid pervious, the liquid pervious top sheet 21 may be configured to be liquid pervious in a predefined region. Alternatively, use can be made of a combination of a liquid pervious top sheet 21 and a patterned liquid impervious sheet. It is possible but not necessary that such liquid impervious sheet is exposed to the surface.

In order to ensure that the subsequent layers are attached to each other, use can be made of a glue material, for instance chosen from natural rubber latex, starch and polyvinyl alcohol. The glue material may be applied as a continuous film, in the form of a patterned film, for instance as strips, but also in a discontinuous manner, but spraying droplets of glue in accordance with a predefined pattern. Suitably, use is made of a glue material that is activated by means of increasing temperature and/or pressure.

For the lamination of the plurality of layers, a roll-to-roll process may be applied as known per se in the art. Alternatively, a batchwise process can be used, wherein a plurality of sheets is applied on top of a carrier and then laminated. Furthermore, it is feasible that a combination is applied, so as to form a sublaminate packages of two or three layers, and thereafter batchwise laminating a plurality of sublaminate packages.

In a fifth step 105, a lamination treatment is carried out. This is in one particular implementation a heat treatment, and/or a pressure treatment. Heat may be provided in the form of a pressing tool that is brought into contact with the laminate. Heat may alternatively be provided by passing the laminate along heated elements, such as heated rollers.

In a sixth step 106, the laminate is further processed, and typically subdivided into individual diaper products. Such diaper products include not merely a diaper for babies, but alternatively sanitary napkins, incontinence guards and the like. The individual diaper products will then be provided to users. In one suitable embodiment, the diaper product is configured as an inlay 'cartridge' for use in combination with a durable fabric of any suitable design. Alternatively, the diaper product is configured for use as such.

Thus, in summary, the present disclosure relates to a diaper comprising a biodegradable top sheet, a biodegradable absorbent core and a biodegradable bottom sheet, wherein the bottom sheet is liquid impervious and wherein the top sheet is configured for transmission of bodily fluids to the absorbent core. The absorbent core comprises a first and a second non-woven layer comprising pulp fibers, and in between thereof a composting-stimulating layer comprising charcoal. The composting-stimulating layer is particularly based on porous charcoal, and suitably further comprises a fiber material. This disclosure also relates to the manufacturing of such a diaper and the use of such a diaper, including the use for collecting and absorbing bodily fluids such as urine and/or blood, and other bodily materials for creating active humus with a carbon content of at least 20%.

The invention claimed is:

1. A diaper comprising a biodegradable topsheet, a biodegradable absorbent core and a biodegradable bottom sheet, wherein the bottom sheet is liquid impervious and wherein the top sheet is configured for transmission of bodily fluids to the absorbent core, wherein the absorbent core comprises a first and a second non-woven layer comprising pulp fibers, and in between thereof a composting-stimulating layer comprising charcoal wherein the composting-stimulating layer is present in an amount of 8-30 wt % based on the total diaper.

2. The diaper as claimed in claim 1, wherein the charcoal is bamboo charcoal.

3. The diaper as claimed in claim 1, wherein the charcoal has an average particle size in the range of 10-50 microns.

4. The diaper of claim 3, wherein the average particle size is 20-30 microns.

5. The diaper as claimed in claim 1, wherein the composting-stimulating layer further comprises a fiber material.

6. The diaper as claimed in claim 5, wherein the fiber material is a pulp material.

7. The diaper as claimed in claim 5, wherein the composting-stimulating layer is in the form of a sheet.

8. The diaper as claimed in claim 1, wherein the first and second non-woven layers each comprises fiber particles prepared from reed material.

9. A method of manufacturing a diaper as claimed in claim 1, comprising the steps of:
providing a biodegradable, liquid impervious backsheet;
providing thereon a layer of non-woven pulp fibers;
providing thereon a composting-stimulating layer comprising charcoal;
providing thereon another layer of non-woven pulp fibers, and
providing thereon a biodegradable and liquid pervious topsheet.

10. The method as claimed in claim 9 comprising sealing of the topsheet and the bottom sheet in a thermal treatment.

11. A diaper comprising a biodegradable topsheet, a biodegradable absorbent core and a biodegradable bottom sheet, wherein the bottom sheet is liquid impervious and wherein the top sheet is configured for transmission of bodily fluids to the absorbent core, wherein the absorbent core comprises a first and a second non-woven layer comprising pulp fibers, and in between thereof a composting-stimulating layer comprising charcoal wherein the composting-stimulating layer further comprises coffee grounds present in an amount of 10-40% relative to the charcoal.

12. The diaper as claimed in claim 11, wherein the coffee grounds contain grounds of caffeine-free coffee.

13. The diaper as claimed in claim 11, wherein the composting-stimulating layer is present in an amount of 8-30 wt % based on the total diaper.

14. The diaper as claimed in claim 11, wherein the charcoal is bamboo charcoal.

15. The diaper as claimed in claim 11, wherein the composting-stimulating layer further comprises a fiber material.

16. The diaper as claimed in claim 11, wherein the first and second non-woven layers each comprises fiber particles prepared from reed material.

17. A diaper comprising a biodegradable topsheet, a biodegradable absorbent core and a biodegradable bottom sheet, wherein the bottom sheet is liquid impervious and wherein the top sheet is configured for transmission of bodily fluids to the absorbent core, wherein the absorbent core comprises a first and a second non-woven layer comprising pulp fibers, and in between thereof a composting-stimulating layer comprising charcoal wherein the first and second layers each comprises fiber particles prepared from reed material.

18. The diaper as claimed in claim 17, wherein the fiber particles in the first layer that is arranged adjacent to the topsheet, has an average particle size of less than 3 mm.

19. The diaper as claimed in claim 17, wherein the fiber particles in the second layer that is arranged adjacent to the bottom sheet has a fiber particle diameter in the range of 1-5 mm.

* * * * *